United States Patent [19]
Joshi et al.

[11] Patent Number: 5,567,287
[45] Date of Patent: Oct. 22, 1996

[54] GAS RELEASING ELECTROCHEMICAL CELL FOR FLUID DISPENSING APPLICATIONS

[75] Inventors: Ashok V. Joshi; John H. Gordon; Yousheng Shen, all of Salt Lake City, Utah

[73] Assignee: Ceramatec, Inc., Salt Lake, Utah

[21] Appl. No.: 495,211

[22] Filed: Jun. 27, 1995

Related U.S. Application Data

[60] Division of Ser. No. 301,116, Sep. 6, 1994, Pat. No. 5,427,870, and a continuation-in-part of Ser. No. 58,438, May 7, 1993, Pat. No. 5,454,922.

[51] Int. Cl.$^6$ ........................................... C25B 9/00
[52] U.S. Cl. ........................ 204/265; 204/266; 204/291
[58] Field of Search ................................. 204/252, 265, 204/266, 283, 291, 292, 294; 429/12, 27, 30, 33, 40, 46, 219, 220

[56] References Cited

U.S. PATENT DOCUMENTS

5,454,922 10/1995 Joshi et al. ............................ 204/265

*Primary Examiner*—Bruce F. Bell
*Attorney, Agent, or Firm*—Trask, Britt & Rossa

[57] ABSTRACT

A self-contained device which continuously dispenses a packaged fluid is disclosed. The device is particularly suited for applications where several months may lapse before performance is manually initiated, after which a consistent steady flow is required for an extended period until the packaged fluid is exhausted. The device is particularly suited for applications where ease of fabrication is important. The device utilizes an electrochemically-generated gas, such as oxygen or nitrogen, to pressurize the packaged fluid to dispense it. Oxygen can be electrochemically released from a solid anode material of the general form $A_xO_y$ as A ions migrate across a suitable ion-conducting electrolyte. Alternatively, nitrogen can be the pressurizing gas wherein it is electrochemically released from a solid, anode material of the general form $A'_\alpha N_\beta$ where A' is a cation, as A' ions migrate across a suitable ion-conducting electrolyte. At the cathode, several possibilities may occur, either the migrated cations are reduced to their elemental state, or a solid material, $R_2$, where R is a halogen, is reduced to $R^-$, or solid material, R', where R' is a group VIB element other than oxygen is reduced to $R'^{-2}$, or solid material $CR_x$, is reduced to $C+XR^-$. The released gas, oxygen or nitrogen, pressurizes a chamber resulting in fluid contained in a flexible bladder within the chamber to be forced through an outlet. Depending on the selection of anode and cathode materials, the device will be self driven or else will require a battery to provide a driving force.

8 Claims, 7 Drawing Sheets

GAS RELEASING ELECTROCHEMICAL CELL FOR FLUID DISPENSING APPLICATIONS

This is a continuation of application Ser. No. 08/301,116, filed Sep. 6, 1994, now U.S. Pat. No. 5,427,870 issued Jun. 27, 1995, and further a continuation-in-part of application Ser. No. 08/058,438, filed May 7, 1993, now U.S. Pat. No. 5,454,922.

BACKGROUND OF THE INVENTION

1. Field of the Invention

This invention relates to a dispensing device, in particular a device where the active fluid is oxygen or nitrogen gas which has been released from a solid state electrochemical cell, and where the pressure increase resulting from the release of such gas pushes fluid from a bladder within a pressure-tight chamber through an outlet in a steady continuous flow until the fluid contents of the bladder are exhausted.

2. State of the Art

Richter in U.S. Pat. No. 3,894,538 disclosed a device for dispensing medicines to man or beast. The medicine was contained in a flexible container which became compressed as fluid was electro-osmotically or electrolytically introduced into an adjacent flexible chamber. The rate of medicine discharge was regulated by using a potentiometer.

Maget in U.S. Pat. No. 4,522,698 disclosed electrochemical prime movers. Embodiments of the invention include a device for dispensing pharmaceuticals to a human body over a substantial period of time at a sustained very low rate, where a battery provides the driving force to transport an electrochemically active gas from a precharged chamber to a second chamber through an ion-exchange membrane. Oxygen from air was disclosed as moving across an ion-exchange membrane to pressurize a chamber. Pressure in a chamber increases as electroactive gas transports across the membrane, this increase in pressure drives a piston which forces the contained pharmaceutical fluid to flow through an outlet. The invention requires electrodes which are electrically conductive and act as catalyst to convert molecules to ions; titanium-palladium alloy or palladium black are recommended materials. A controller is utilized to control the magnitude and time pattern of current and voltage applied to the membrane as well as to turn current on and off. To function, the invention requires either exposure to air or precharging with an electroactive gas.

Maget in U.S. Pat. No. 4,886,514 disclosed electrochemically driven drug dispensers. A potential from an external power source drives an electrochemically active gas such as hydrogen or oxygen to be transported across a membrane from a fixed volume chamber to a chamber which has a variable volume. The volume of the chamber varies by either flexing am expansible diaphragm type wall or by displacing a sliding wall, said wall is shared by a second variable volume chamber which contains a fluid drug to be administered. As the electrochemically active gas is transported to the first variable volume chamber, the drug is forced out of the second variable volume chamber through an outlet. Countering the electrochemical transport of gas across the membrane, the gas diffuses in the opposite direction across the membrane in accordance to the pressure gradient and diffusivity properties of the membrane. A controller compensates for the gas diffusion rate and varies the voltage and current to achieve the desired drug delivery rate in a steady or intermittent mode. To function, the invention requires precharging with an electroactive gas.

Maget et al. in U.S. Pat. No. 4,902,278 disclosed a fluid delivery micropump. The pump utilizes an air-actuated battery in a fixed closed circuit with an electrochemical cell which drives the transport of oxygen in air across a membrane. The transport applies external pressure to a collapsible reservoir filled with fluid, as a result, fluid is expelled from the reservoir through an outlet. The membrane is preferably a Nation material (a perfluoro sulfonic polymer) which has been coated with platinum black/10% Teflon. Electrodes are preferably titanium screens. To control the current, a resistor is utilized. The device is activated by removing a protective peel tab to expose air inlet ports to the battery cathode. A disadvantage of this type of system is that shelf life of the device is dependent on the integrity of the seals which prevent air leakage to the battery. If the seals are not perfect, the battery will slowly discharge before the desired time of use. To function, the invention requires exposure to air.

The prior art includes several devices which are capable of performing the general function of the device presently disclosed; however, the prior art has not satisfied a demand which exists for a device which 1) has a design which can dispense a fluid over a nearly constant rate for an extended period of time, 2) has a simple design which is conducive to fabrication, 3) does not require exposure to air, fluid or the precharging of an electrochemically active gas to function, 4) does not utilize polymeric ion-exchange membranes which typically must remain hydrated to some degree to function and which are affected by humidity, which can cause changes in conductivity, gas flow and dispensing rates.

SUMMARY OF THE INVENTION

An invention is disclosed which provides a self-powered, low cost device which has a long shelf life and which dispenses a fluid at a slow, steady, predictable rate over an extended period of time. The fluid itself may have beneficial attributes or it may contain chemicals or nutrients which provide a benefit or which inhibit something undesirable to a system or living organism. The fluid can be delivered to a specific site through appropriate tubing and connections, or the fluid can be delivered to an external portion of the device where it is allowed to evaporate into a room, vehicle, container or other environment surrounding the dispenser. The dispenser may be embodied in a form intended to be stationary, sitting upon something or hung from something, or may be embodied in a form to be worn on a person or animal in the form of a pendant, a clothing attachment, a collar attachment for an animal, or in a form to be hung from a tree or other type of plant. A significant aspect of the invention is that some embodiments of the gas-generating electrochemical cell also act as a battery so that a separate power source is not required, in contrast to prior art devices.

The present device is delivered to consumers in a disabled condition so that no drain on the battery or electroactive components occurs when the device is on the shelf, waiting to be used. Activation occurs when the consumer completes an electric circuit. This may be accomplished in various ways, for example, by snapping electronically conducting components of the device together or by removing a temporary insulator from between two electronic contacts. In addition, the user typically unseals the fluid sack outlet by removing a plug, or by cutting or by puncturing the sack. Thus, neither the power supply nor the fluid contents will be compromised before the device is to be utilized.

A novel solid state electrochemical cell releases oxygen or nitrogen gas which is the working substance, i.e., pumping gas in the device. Released gas flows into a gas-tight chamber which encloses a flexible bladder containing the fluid to be dispensed. As gas is transported into a gas-tight chamber, the resulting increase in pressure compresses the bladder such that the fluid flows through an outlet to the desired destination or to a site on the dispenser where the fluid can evaporate or disperse.

Oxygen is a suitable pressurizing gas and can be electrochemically released from a solid anode material of the general form $A_xO_y$. The value of x is 1 to 3 and y is 1 to 4. Nitrogen also may be a suitable pressurizing gas. It can be electrochemically released from a solid anode material of the general form $A'_\alpha N_{\beta 2}$. The value of $\alpha$ is 1 to 3 and $\beta$ is 1 to 3. In each of the above instances, an ion migrates across a suitable ion conducting electrolyte. The migrating ion may be, respectively, A ions or A' ions. A is a cation such as silver, copper and the like in a positive valence state, while A' is an alkali metal such as sodium, lithium and the like in a positive valence state. The migrating ion (cation) allows the anion ($O^{-2}$ or $N^{-3}$) to combine with a similar anion to form a gas ($O_2$ or $N_2$) concomitant with the release of electrons. At the cathode, several possibilities may occur, examples include ones in which the migrated cations are reduced to their elemental state, or where a solid material $R_2$ wherein R is a halogen is ionizable to $R^-$, or solid material, R', where R' is a group VIB element reducible to $R'^{-2}$ or where cathode material $CR_x$ is reduced to $C+XR^-$. A typical $CR_x$ is a fluorocarbon such as a $CF_x$ which is readily available. In the above formulas, X and x are equivalent and have a value of about 0.8 to about 1.2. The driving force powering the device is either provided by the electrochemical reactions occurring during operation of the cell, or by a battery.

The micropumps of the instant invention are characterized by a fluid dispensing chamber wherein the chamber has a fluid reservoir and a gas space. The gas space and fluid reservoir are separated by a flexible material, e.g., a membrane or a bladder, such that as the gas space expands due to incoming gas, the fluid reservoir is caused to shrink which causes fluid, generally liquid, to be discharged from a discharge port in the reservoir.

DETAILED DESCRIPTION OF THE INVENTION

The instant invention employs anode materials wherein an electrochemical decomposition occurs at the anode to release an anion such as $O^{-2}$ or $N^{-3}$ which, upon release of electrons, combine to form $O_2$ and $N_2$ gases which can be used for pressurizing purposes. The anode materials generally comprise a compound formed of a metal cation, typically monovalent, and a divalent or trivalent anion such as $O^{-2}$ or $N^{-3}$. The cathode material is one which electrochemically reacts with the cation species from the anode material after its transport through an appropriate electrolyte. The electrolyte maybe solid, liquid or a solid dissolved in a liquid. If the electrolyte is not solid, a separator such as the microporous separators used in the battery industry may be used to prevent direct contact of the anode and cathode materials. If a separator is used, electrolyte is absorbed into the pores of the separator. Battery separators are typically a microporous sheet of polyolefin such as ethylene vinyl alcohol copolymers having a pore size less than 1.0 micron. The copolymer has a linear-type olefin portion with a vinyl alcohol content of between 20 and 90%. The alcohol portion may also be hydrolyzed. Other typical battery separators include those described in the patent literature such as cellophane with a grafted polymer U.S. Pat. No. 3,330,702; cellulosic material or paper coated with a resin U.S. Pat. Nos. 3,893,871 and 3,976,502; cellophane with a grafted copolymer U.S. Pat. No. 3,330,702; methacrylic acid-divinyl benzene copolymer U.S. Pat. No. 3,684,580; phenol-resorcinol-formaldehyde resin U.S. Pat. No. 3,475,355; and polyacrylamide U.S. Pat. No. 3,018,316. Several examples of a polyolefin-homo or copolymer film with fillers are U.S. Pat. Nos. 3,870,586; 3,955,014; 3,985,580; and U.S. Pat. No. 4,024,333. The use of polytetrofluoroethylene is described in U.S. Pat. No. 3,475,222 and U.S. Pat. No. 3,661,645, while other polyvinyl compositions are found in U.S. Pat Nos. 3,585,081; 3,766,106; 3,875,270 and 3,907,601. Silicone rubber-vinyl copolymer is still yet another example of a battery separator described in U.S. Pat. No. 3,585,081. The gas producing electrochemical cell is sealed from the external environment.

Since no gaseous materials are involved in the cathode chamber, the cathode or cathode current collector need not be porous. A preferred cathode is one which is sealed from the environment and has a combination of properties such that unreacted cathode and reacted cathode materials have adequate ionic and/or electronic conductivity such that the voltage drop across the zone does not increase significantly relative to the rest of the cell as the cell discharges. Suitable cathodes are set forth in the following examples.

In prior gas producing cells, it was typical for the cathode and anode chamber to contain an element common to each. For example, in Maget patent ('698), the cathode contained $O_2$ and the anode contained oxygen in combined form, $H_2O$, to form an $O_2/H_2O$ redox couple with a proton transported through an electrolyte so that the reaction on opposite sides of the electrolyte were the reverse of one another. The total redox energy involved is zero, however, because of internal cell resistance, electrode polarization, and differences in oxygen partial pressure, a battery (power source) had to be used in such cells. Also, in such a cell, a gas is present at both electrodes, thereby requiring porous electrodes.

In the instant invention, many cells have completely different materials, i.e., no common elements, in the cathode and anode chambers. Thus, in many instances a net energy production (positive voltage) occurs so that the cell is self-powered.

The device disclosed herein is particularly distinguished from the prior art in that the device can function while completely sealed from its external environment, excluding the outlet port through which the fluid will be dispensed, and without requiring an internal reservoir of gas to be pumped. Unlike the devices described in the prior art, an organic ion-exchange membrane is not utilized in this device, and since the device is sealed, this device is not sensitive to changes in ambient humidity. Also, the device does not rely on access to air or other gas to operate. Further, because the device is simply structured and is comprised of readily available, easily fabricated materials, it is disposable.

The following examples illustrate different possibilities of the device where the anode and cathode couple, in effect, create a galvanic cell such that an additional battery is not required:

EXAMPLE 1

An example of an oxygen releasing, solid, self-driving cell is one in which the active anode material is $Ag_2O$ and the active cathode material is solid $I_2$ or a combination solid $I_2$ and poly(2-vinylpyridene) (P2VP) or poly 2 vinylquinoline (P2VQ) which combine to form a material both electronically and ionically conductive. Several silver ion conductors are suitable as solid electrolytes for this application including $Ag_4RbI_5$, $AgI/Al_2O_3$ and Ag-Nasicon; however the preferred electrolyte in this case is AgI which reactively forms at the interface between the anode ($Ag_2O$) and cathode ($I_2$) layers. This electrolyte forms spontaneously as an interfacial reaction, requires no preparation, and conforms to any irregularities in the interface. The electrochemical reactions are:

| Anodic: | $Ag_2O \rightarrow 2Ag^+ + \frac{1}{2}O_2 + 2e^-$ |
| --- | --- |
| Cathodic: | $2Ag^+ + I_2 + 2e^- \rightarrow 2AgI$ |
| Overall: | $Ag_2O + I_2 \rightarrow 2AgI + \frac{1}{2}O_2$ |

Figure 8A:
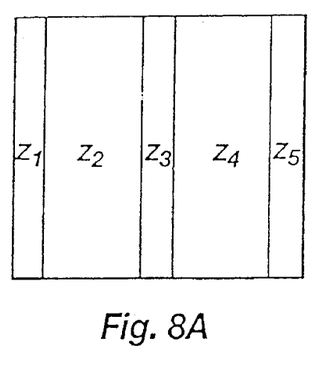
FIG. 8A schematically illustrates an electrochemical cell of the invention in a pre-discharged condition.
Figure 8B:
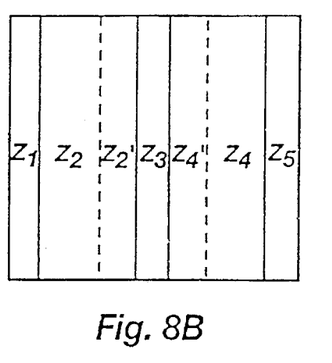
FIG. 8B schematically illustrates a discharging cell.
Figure 8C:
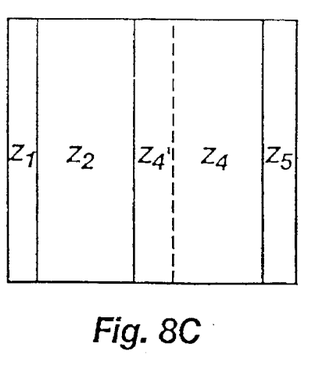
FIG. 8C schematically illustrates a cell which does not require a discrete electrolyte member.

Such a cell has a standard potential, E°, of 0.96 V; therefore, in this case, no battery or other applied voltage source is required to drive the process. Once the electrical circuit is completed between the cathode and the anode, electrons and ions begin to flow and the device is operable. Other materials which would release oxygen when properly coupled with $I_2$ include $Na_2O$, $K_2O$, $Na_2O_2$, $Ag_2O_2$, $K_2O_2$, $Rb_2O$ and $Rb_2O_2$. A cell of this type is schematically illustrated in FIG. 8. The cell remains dormant until an electron conductor is connected between the anode and cathode materials.

EXAMPLE 2

Another example of an oxygen releasing, solid cell which is self-driving is one in which the anode material is $Ag_2O$ and the cathode material is solid S or a combination of solid S and $Ag_2S$ which together form a material both electronically and ionically conductive. A suitable electrolyte is $Ag_4RbI_5$. The electrochemical reactions are:

| Anodic: | $Ag_2O \rightarrow 2Ag^+ + \frac{1}{2}O_2 + 2e^-$ |
| --- | --- |
| Cathodic: | $2Ag^+ + S + 2e^- \rightarrow Ag_2S$ |
| Overall: | $Ag_2O + S \rightarrow Ag_2S + \frac{1}{2}O_2$ |

Such a cell has a standard potential, E°, of 0.16 V. Other materials which could be used in the place of S are Se and Te.

EXAMPLE 3

An example of a nitrogen releasing, solid, self-driving cell is one in which the anode material is $Li_3N$ and the cathode material is solid $I_2$ or a combination of solid $I_2$ and poly(2-vinylpyridene) which combine to form a material both electronically and ionically conductive. Several lithium ion conductors are suitable as solid electrolytes for this application including $LiI/Al_2O_3$ and Li-Nasicon; however, the preferred electrolyte in this case is LiI which forms at the interface between the anode and cathode layers. This electrolyte, similarly to AgI, forms spontaneously, requires no preparation, and conforms to any irregularities in the interface. The electrochemical reactions are:

| Anodic: | $Li_3N \rightarrow 3Li^+ + \frac{1}{2}N_2 + 3e^-$ |
| --- | --- |
| Cathodic: | $3Li^+ + \frac{3}{2}I_2 + 3e^- \rightarrow 3LiI$ |
| Overall: | $Li_3N + \frac{3}{2}I_2 \rightarrow 3LiI + \frac{1}{2}N_2$ |

Such a cell has a standard potential, E°, of 2.16 V; therefore, in this case, no battery or other applied voltage source is required to drive the process. Once the anode and cathode are electronically connected, the cell will begin to function.

EXAMPLE 4

Another example of a nitrogen releasing, solid, self-driving cell is one in which the anode material is $NaN_3$ and the cathode material is solid $I_2$ or a combination of solid $I_2$ and poly(2-vinylpyridene) which combine to form a material both electronically and ionically conductive. Several sodium ion conductors are suitable as solid electrolytes for this application including $NaI/Al_2O_3$ and Nasicon; however the preferred electrolyte in this case is NaI which forms at the interface between the anode and cathode layers. This electrolyte forms spontaneously, requires no preparation, and conforms to any irregularities in the interface. The electrochemical reactions are:

| Anodic: | $NaN_3 \rightarrow Na^+ + \frac{3}{2}N_2 + e^-$ |
| --- | --- |
| Cathodic: | $Na^+ + \frac{1}{2}I_2 + e^- \rightarrow 3LiI$ |
| Overall: | $NaN_3 + \frac{1}{2}I_2 \rightarrow NaI + \frac{1}{2}N_2$ |

Such a cell has a standard potential, E°, of 4.05 V; therefore, in this case, no battery or other applied voltage source is required to drive the process.

The following examples illustrate different possibilities of the device where the solid anode and cathode couple require an applied voltage to drive the gas releasing reaction, such an applied voltage can be provided by one or more batteries:

EXAMPLE 5

Another example of a nitrogen releasing cell which is self driving is one in which the anode material is $Li_3N$ and the cathode material is polycarbon monofluoride of $CF_x$ (where x is 0.8 to 1.2). An example of such a material is a product of Allied Chemical under the trade name Accuflor™. A suitable electrolyte is a 1:1 mixture of ethylene glycol dimethyl ether and propylene carbonate containing 1M $LiBF_4$. This electrolyte is used with a thin microporous separator comprised of polypropylene or polyolefin. Such a separator is electronically insulative but has high ion permeability. The cell is similar to the Li-$CF_x$ battery described in Modern Battery Technology by C. D. S. Tuck, pp. 337–348, except that in the case of this invention, the lithium anode is replaced by a lithium nitride anode so that gas is released electrochemically as the cell discharges. The electrochemical reactions are:

| Anodic: | $x\ Li_3N \rightarrow 3x\ Li^+ + x/2\ N_2 + 3x\ e^-$ |
|---|---|
| Cathodic: | $3x\ Li^+ + 3\ CF_x + 3x\ e^- \rightarrow 3x\ LiF + 3\ C$ |
| Overall: | $x\ Li_3N + 3\ CF_x \rightarrow 3x\ LiF + 3\ C + x/2\ N_2$ |

Such a cell has a standard potential, $E°$, of approximately, 2.7 V; therefore, in this case, no battery or other applied voltage source is required.

EXAMPLE 6

Another example of a oxygen releasing cell which is self driving is one in which the anode material is $Ag_2O$ and the cathode material is polycarbon monofluoride of $CF_x$ (where x is 0.8 to 1.2). An example of such a material is a product of Allied Chemical under the trade name Accuflor™. A suitable electrolyte is 1:1 mixture of ethylene glycol dimethyl ether and propylene carbonate containing 1M $AgBF_4$. This electrolyte is used with a thin microporous separator comprised of polypropylene or polyolefin.

EXAMPLE 7

Another example of a oxygen releasing cell which is self driving is one in which the anode material is a paste consisting of $Ag_2O$ silver nitrate and sodium hydroxide solution and the cathode material is a paste consisting of solid S, carbon, and silver nitrate, and where the anode and cathode are separated by a solid polymer electrolyte which has been exchanged with silver ion containing solution such as silver nitrate.

EXAMPLE 8

An example of an oxygen releasing, solid cell which is not self-driving and which would require a battery or other applied voltage source is one in which the anode material is $Cu_2O$ and the cathode material is porous copper or graphite or carbon. Several copper ion conductors are suitable as solid electrolytes for this application including $Rb_4Cu_{16}I_7Cl_{13}$ or Cu-Nasicon or a mixture of CuI and $Al_2O_3$. The electrochemical reactions are:

| Anodic: | $Cu_2O \rightarrow 2Cu^+ + \frac{1}{2}O_2 + 2e^-$ |
|---|---|
| Cathodic: | $2Cu^+ + 2e^- \rightarrow 2Cu$ |
| Overall: | $Cu_2O \rightarrow 2Cu + \frac{1}{2}O_2$ |

Such a cell has a standard potential, $E°$, of −0.77 V. Other oxygen releasing solid couples include $Cu_2O/I_2$, $Li_2O/I_2$, $Na_2O/S$, $K_2O_2/S$.

Regardless of whether the cell is self-driven or driven with a battery or other applied voltage source, the rate of fluid dispensing is directly proportional to the rate of oxygen or nitrogen, in the above stated examples, released at the anode which is directly proportional to the electrical current. The electrical current required to dispense the fluid is very low, about 183 µA per ml fluid per day at standard conditions for the oxygen releasing cells mentioned above assuming no leakage occurs from the gas chamber. To determine actual fluid delivery at conditions other than standard for those cells, the following relationship can be used:

ml actual per day=$0.00349 \times Z \times C \times T/P$;
where:

Z=Number of electrons which must pass though the device circuit per molecule of gas released. Typically Z=4 for $O_2$ release, Z=6 for $N_2$ release.

C=Current in µA (microamps),

T=Temperature in degrees K

P=Pressure in Torr

Many applications involving concentrated chemicals will require substantially less than 1 ml per day to be effective, thus total current flow in the range of five to 500 µA would be typical for this device although the device is not limited to this range. Such a current range would provide fluid delivery ranges from 0.03–2.7 ml per day. Thus, this device is effective when operating at low current densities. If a self-driven cell is selected, resistors and controllers to restrict or otherwise control current flow may be utilized or may be avoided by adjusting cement density through cell design.

Without complicating the present device, several strategies can be taken to make adjustments in construction such that the desired substance dispensing rate is achieved. Some strategies relate to adjustments which would affect the current density and hence the rate of fluid flow. The area of the electrolyte surface can be predetermined or the thickness of the electrolyte may be varied in a particular cell to give a desired gas discharge rate and consequently a desired fluid flow. The rate of cell discharge can be increased by adding constituents to the anode which would improve the electronic and ionic conductivity. For example, the addition of $Ag_2S$ and/or $RbAg_4I_5$ to the anode has been found to dramatically improve cell discharge rates. A combination of 20% by weight of each was very effective. Other concentrations are also effective. Addition of electrolytes dissolved in non-aqueous electrolytes to either anode or cathode have similar effects and help prevent polarization. The addition to the anode of a small amount of oxygen evolution catalyst such as 0.5% RuO2 or IrO2 can increase the discharge rate by an order of magnitude. Larger and smaller amounts of these oxides also may be effectively used.

Further advantages of the invention will become apparent from the drawings and more detailed description below.

Figure 1:
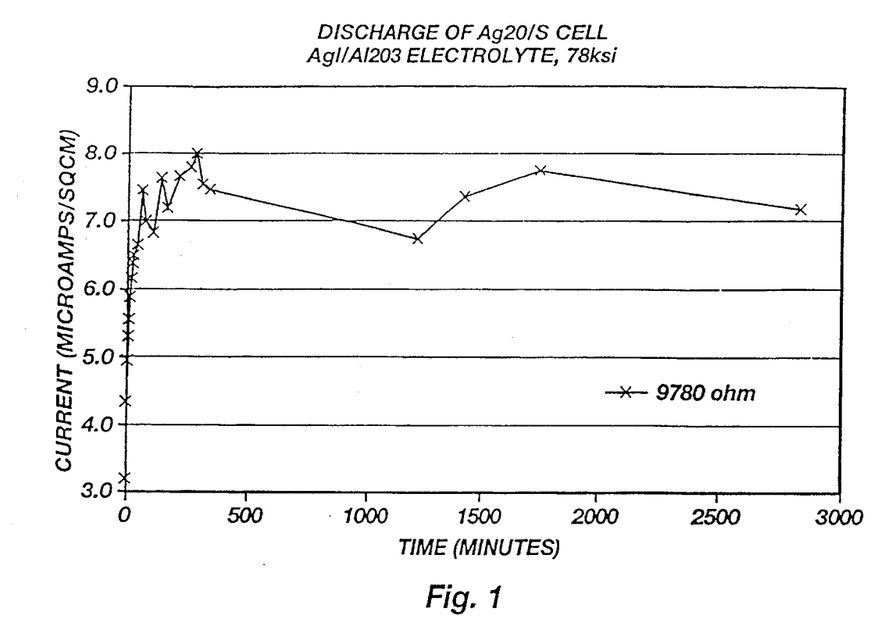
FIG. 1 shows a plot of current density versus time of an $Ag_2O/S$ cell.

FIG. 1 shows a plot of current density versus time of a $Ag_2O/S$ cell. Finely divided AgI (40%) and high surface area $Al_2O_3$ (60% by weight) were heated to 500° C. to form a very ionically conductive electrolyte. A small amount of this electrolyte was pressed to form a thin membrane in a 0.625" diameter die. An anode mixture of $Ag_2O$ powder, graphite powder, and AgI+$Al_2O_3$ electrolyte was added to one side of the membrane, a cathode mixture of sulfur powder, graphite powder, and AgI+$Al_2O_3$ electrolyte was added to the other side of the membrane. The entire cell was pressed into a three layer pellet at a pressure of 78,000 psi. A perforated stainless steel plate was used for the anode contact and an un-perforated stainless steel plate was used for the cathode contact. Total height of the cell was about 0.25 inches. The cell circuit was completed by contacting an electronic resistor to the anode and cathode contacts. A resistor of approximately 10000 ohms was used in the circuit.

Figure 2:
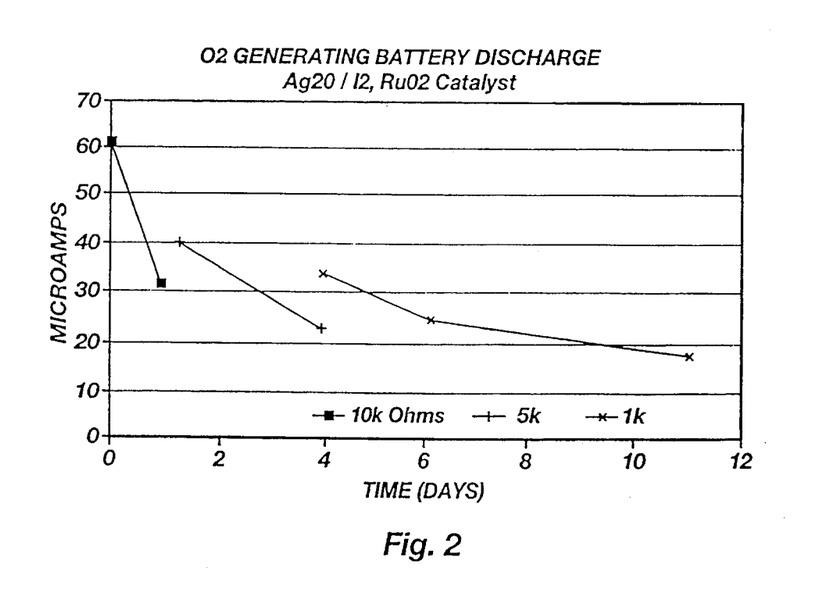
FIG. 2 shows a plot of current versus time of an $Ag_2O/I_2$ cell.

FIG. 2 shows a plot of current versus time of a $Ag_2O/I_2$ cell where the anode was approximately 60% $Ag_2O$, 20% $Ag_2S$, 20% $Ag_4RbI_5$ and 0.5% $RuO_2$ while the cathode was 6.7% P2VP with the balance consisting of $I_2$. Percents stated are percents by weight. The cathode mixture was heated slightly to form a semi-plastic paste. First the anode mixture was pressed in a 0.75" diameter die at about 20,000 psi. The electrolyte between the anode and cathode was AgI which formed in situ when the anode and cathode were pressed together. The reaction continues until a continuous, impervious layer of AgI is formed, which sets as a separator between the reactive materials.

A perforated stainless steel plate was used for the anode contact and an unperforated stainless steel plate was used for the cathode contact. Total height of the cell was about 0.2". The cell circuit was completed by contacting an electronic resistor to the anode and cathode contacts. Resistors of 10000 ohms, 5000 ohms and 1000 ohms were used in the circuit.

Figure 3:
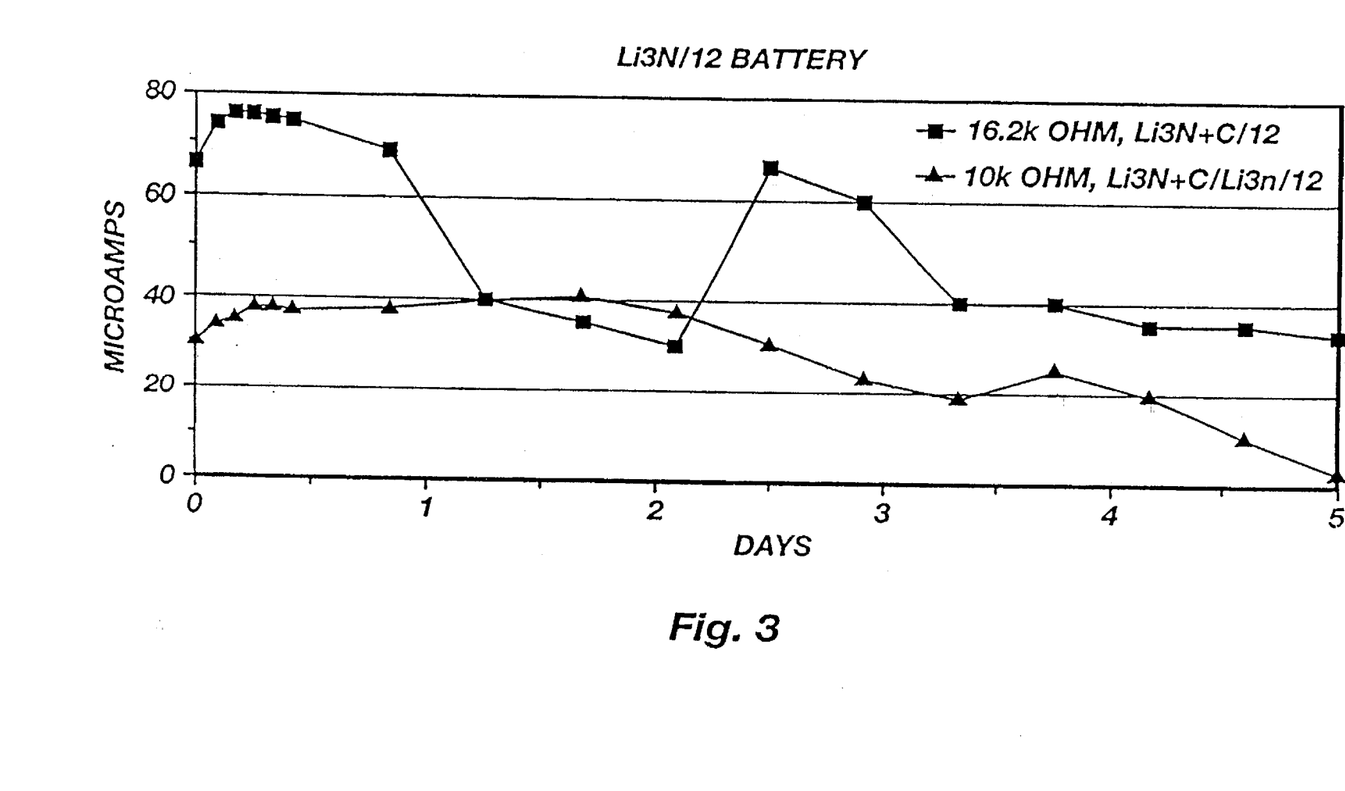
FIG. 3 shows a plot of current versus time of two $Li_3N/I_2$ cells.

FIG. 3 shows a plot of current versus time of two $Li_3N/I_2$ cells. In the first cell approximately 33% graphite powder was mixed with a balance of $Li_3N$. Some of this mixture was pressed in a 0.75" diameter die at approximately 20,000 psi. A cathode mixture of 5% P2VP with balance $I_2$ was mixed in a ball mill with alumina balls overnight. This cathode mixture was not heated. Some of this mixture was pressed onto the cathode. A continuous, thin LiI electrolyte layer formed in situ between the anode and cathode when they were pressed together.

A perforated stainless steel plate was used for the anode contact and an unperforated stainless steel plate was used for the cathode contact. Total height of the cell was about 0.2". The cell circuit was completed by contacting an electronic resistor of 16,200 ohms to the anode and cathode contacts. In a second $Li_3N/I_2$ cell, approximately 33% graphite powder was mixed with a balance of $Li_3N$ powder. Some of this mixture was pressed in a 0.75" diameter die at approximately 20,000 psi. Next a layer of $Li_3N$ powder without graphite was pressed onto the previous layer. On this layer was pressed a cathode mixture of 5% P2VP with balance $I_2$ which had been mixed in a ball mill with alumina balls overnight. A thin, continuous LiI electrolyte layer formed spontaneously in situ between the anode and cathode when they were pressed together. Again, a perforated stainless steel plate was used for the anode contact and an unperforated stainless steel plate was used for the cathode contact. Total height of the cell was about 0.2". The cell circuit was completed by contacting an electronic resistor of 10000 ohms to the anode and cathode contacts.

Figure 4:
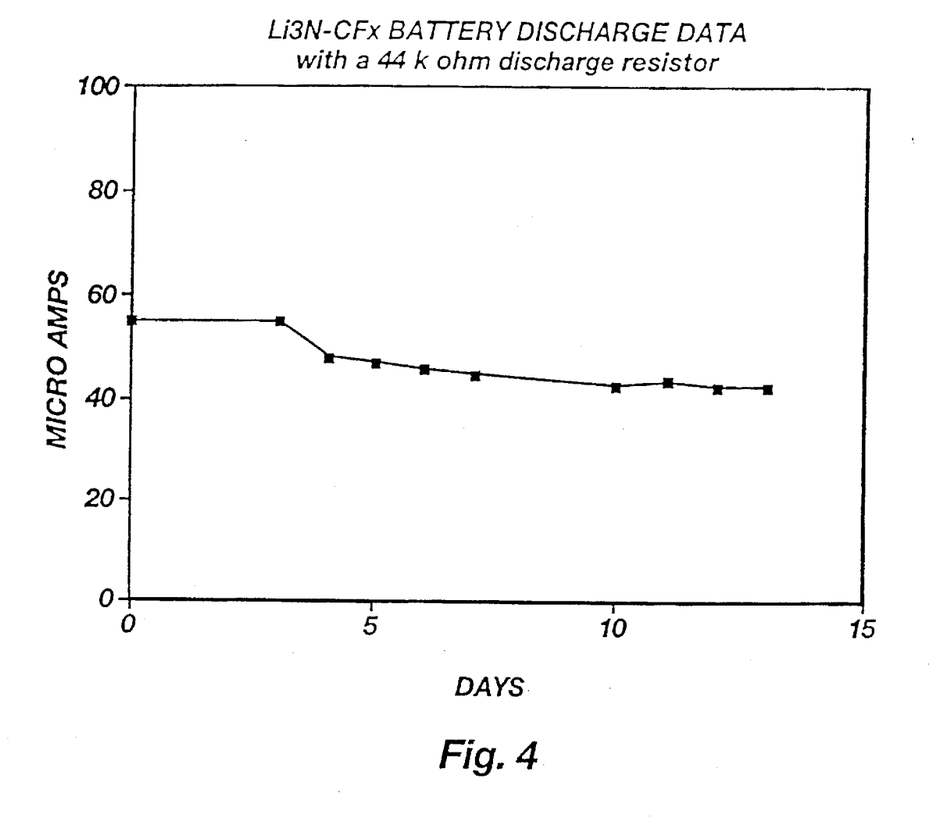
FIG. 4 shows a plot of current versus time of a $Li_3N/CF_x$ cell.

FIG. 4 illustrates the current versus time characteristics for a $Li_3N$—$CF_x$ all in which the anode material was a mixture of 75 wt % lithium nitride ($Li_3N$, Aldrich, Milwaukee, Wis,) and 25 wt % carbon black (Vulcan). To prepare anode material, powders of Li3N and carbon were dry mixed in a ball mill under $N_2$ atmosphere, and then passed through a sieve with a mesh size of 200 microns before pressing into anode pellet (15 mm dia.×3 mm thick).

Cathode material was a mixture of 77 wt % carbon monofluoride ($CF_x$, x between 0.8 to 1.2, Allied Signal Chemicals, Morristown, N.J.), 13 wt % carbon black (Vulcan), and 10 wt % poly-tetrafluoroethylene (PTFE, Aldrich, Milwaukee, Wis.). For preparing the cathode material, powders of CFx, PTFE and carbon were slurried in an isopropanol solution. The slurry was well mixed, heated at 90° C. to coagulate PTFE, and then dried at 100° C. and passed through a sieve with a mesh size of 200 microns before pressing into a cathode pellet (15 mm dia.×5 mm thick).

Liquid electrolyte was 1M lithium fluoroborate ($LiBF_4$, Fluka, Buchs, Switzerland) dissolved in a 1:1 mixture of ethylene glycol dimethyl ether (Aldrich, Milwaukee, Wis.) and propylene carbonate (Aldrich, Milwaukee, Wis.).

Separator material was a hydrophobic microporous polyolefin membrane (Pall RAI Manufacturing Company, Hauppauge, N.Y.). Nickel mesh was used as current collectors.

Figure 5:
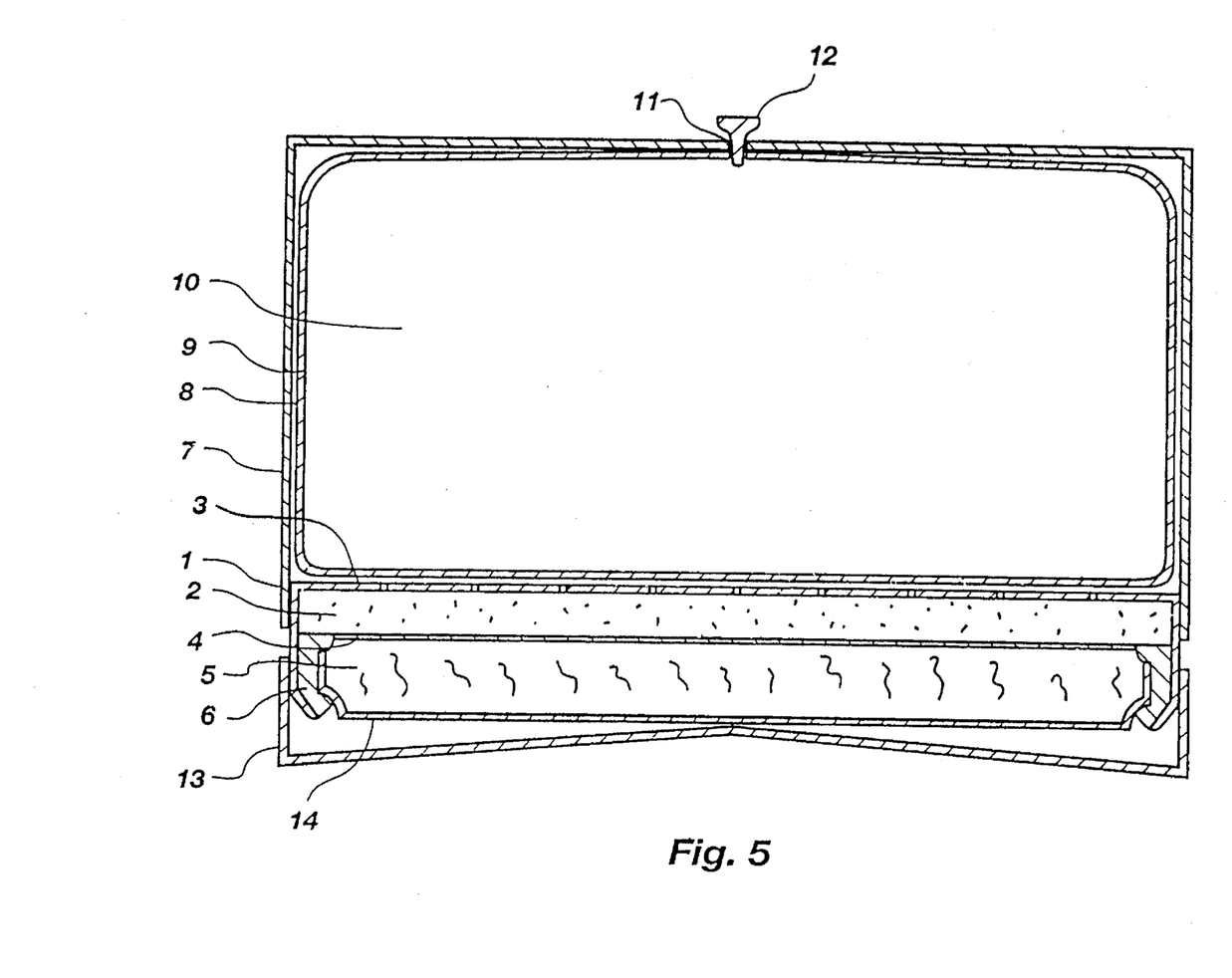
FIG. 5 is a perspective sectional view of a fluid dispensing micropump embodying features of the present invention.

For purposes of illustration of the present invention, an embodiment of the solid electrolyte fluid dispensing micropump is shown in FIG. 5.

Pump housing 1 is fabricated of a chemically resistant and electronically conductive material such as 304 or 316 stainless steel. Gas passages 3 or holes are perforated through the pump housing 1. Anode material 2 is pressed into the pump housing 1. Anode material 2 is comprised of an oxidized compound of the general formula $A_xO_y$ such as $Ag_2O$ or a nitride compound of the general formula $A'_\alpha N_\beta$ combined with other constituents which improve electronic and ionic conductivity and which are electrocatalysts. On top of said anode material, solid electrolyte material 4 is pressed or otherwise forms spontaneously when anode and cathode materials are contacted as indicated hereinabove. The composition of said solid electrolyte material is selected based on the cation A or A' which is to be conducted. For example, AgI mixed with $Al_2O_3$ or $Ag_4RbI_5$ or Ag-Nasicon could be selected to conduct $Ag^{+1}$ cations, or AgI, an $Ag^+$ conductor will form spontaneously when $Ag_2O$ is contacted with $I_2$ to form an electrolytic interface. Cathode material 5 comprised of solid halogen material such as $I_2$ mixed with poly(2-vinylpyridene), or S mixed with $Ag_2S$ and $Ag_4RbI_5$, is pressed into the cathode cap 14 which is an electronic conductor such as 304 or 316SS. A spacer 6 comprised of an electrically insulating material separates the cathode material 5 and cathode cap from the pump housing 1. The cathode cap 14 and the spacer 6 are crimped by the pump housing 1 to form a seal. The gas shell 7 is attached to the pump housing 1. The gas chamber 8 is bounded by the gas shell 7 and the pump housing 1. Within said gas chamber is a fluid sack 9 which contains the fluid to be dispersed 10. Said fluid sack is made of a flexible material, such as Barex or ethylene vinyl alcohol film, which has adequate corrosion properties for said fluid. Said fluid sack has an outlet 11 which passes through said gas shell and is sealed thereto. The fluid sack is preferably a polymeric, filmy, material impervious to both the pressurizing gas molecules and the fluid material.

The fluid sack outlet 11 may be very simple or may have a fitting for the attachment of tubing, or may have an attachment suitable for promoting evaporation of the fluid into the surrounding air. Said fluid sack be may sealed from the external environment before the time of activation with a plug 12, clip or other means, or may have a sealed portion which protrudes through said outlet which is cut off or punctured by the user at the time of activation. Contact clip 13 fabricated of an electronic conductor completes the electrical circuit between said anode contact and said cathode contact after activation by the user. At the time of activation, cations migrate from said anode material to said cathode material to form compound AR, $AR_{x/2y}$ or $A'R_{\alpha/3\beta}$ which remain with cathode material 5. Gas is released from anode material 2, passes through gas passages 3, and enters gas chamber 8. As gas enters said gas chamber, the pressure increases, forcing fluid 10 to be dispensed from fluid sack 9. The thickness of said electrolyte and the cross-sectional area of the active electrochemical cell formed by this device are selected so that the desired fluid dispensing rate is achieved. Optionally, an electronic resistor (not shown) may be placed between the contact clip 13 and cathode cap 14 to modulate the current and dispensing rate to a lower level if desired.

Figure 6:
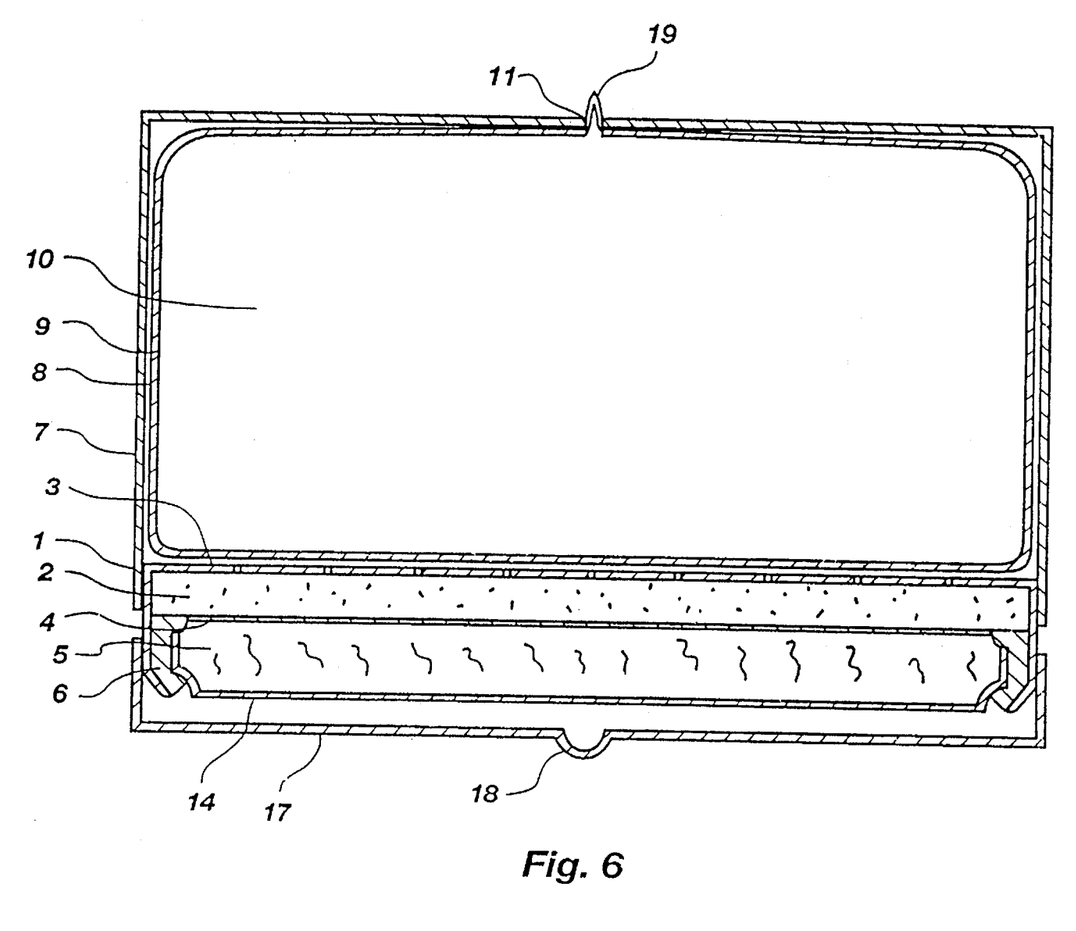
FIG. 6 shows a perspective sectional view of an embodiment of the invention which is a variation of what was shown in FIG. 1.

FIG. 6 shows a perspective sectional view of an embodiment of the invention which is a variation of what was shown in FIG. 1. Those features similar to features in FIG. 1 are similarly numbered. In this embodiment, contact clip 17 is stationary. The device is activated by the user by pressing on tab 18 which inverts to make contact with cathode 5. Another feature variation is shown in this embodiment; a fluid sack 9 is sealed at the outlet 19. At the time of activation, the user cuts or punctures said outlet so that the fluid 10 contained can be dispensed as the device operates.

Figure 7:
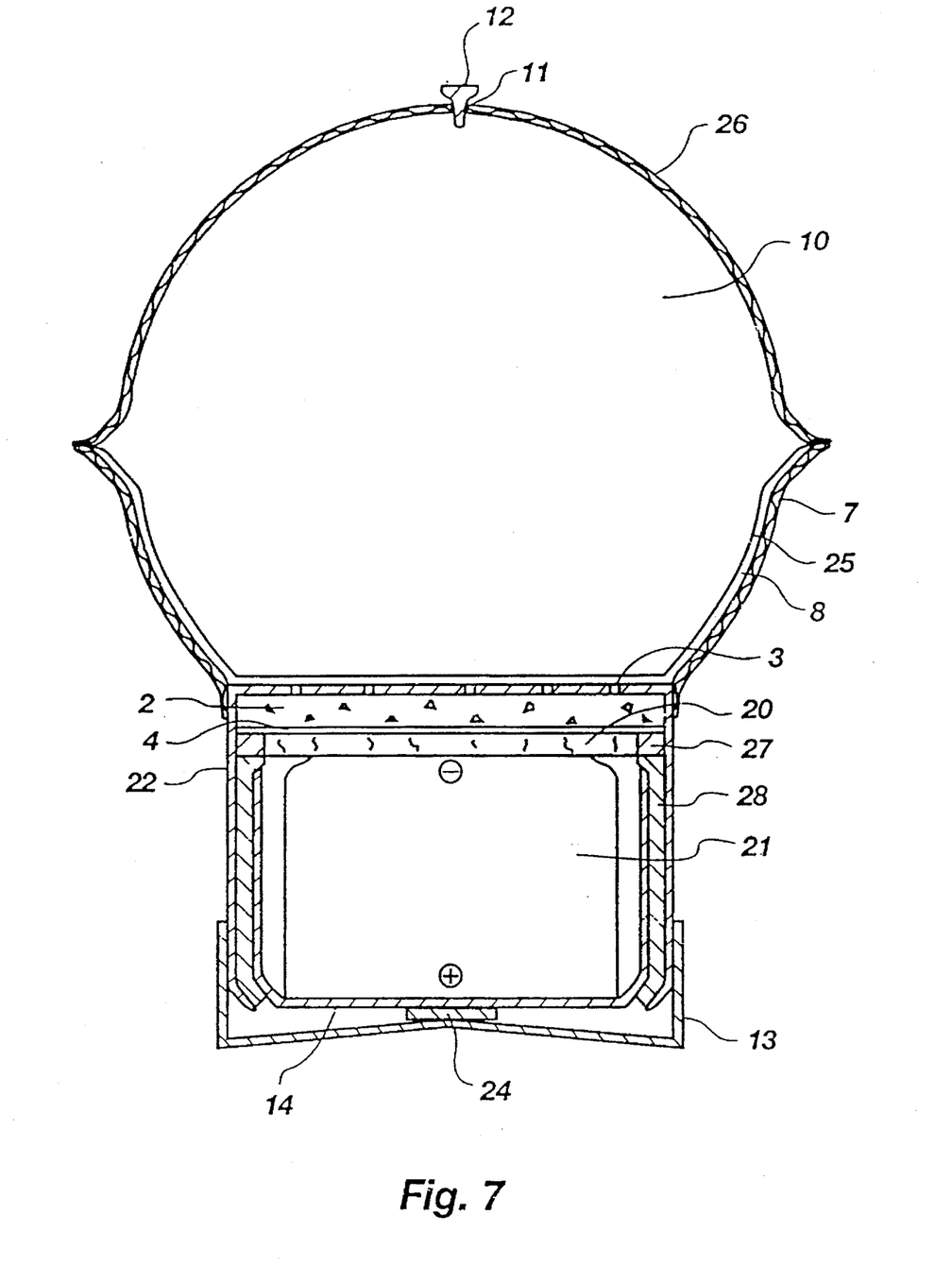
FIG. 7 shows a perspective sectional view of an embodiment of the invention which features a battery integrated into the design.

FIG. 7 shows a perspective sectional view of an embodiment of the invention which features a battery integrated into the design. Those features similar to features in FIGS. 1 and 2 are similarly numbered. Pump housing 22 is fabricated of a chemically resistant and electronically conductive material. Into said pump housing is pressed anode material 2 comprised of a chemically inert, electronically conductive material such as graphite or carbon fibers mixed with an oxidized compound of the general formula, $A_xO_y$ or $A'_{\alpha}N_{\beta 2}$ such as $Cu_2O$. A solid electrolyte material 4 is pressed onto the anode material 2.

The composition of said solid electrolyte material is selected based on the cation A or A' which is to be conducted. For example, $Rb_4Cu_{16}I_7Cl_{13}$, CuI mixed with $Al_2O_3$, or Cu-Nasicon could be selected to conduct $Cu^{+1}$ cations. Cathode material 20, comprised of an electronic conductor such as graphite fiber or copper or reducible material such as $I_2$ or S mixed with an electronic conductor and ionic conductor, is pressed against solid electrolyte 4. A spacer 27 comprised of an electrical insulator prevents contact between the cathode 20 and the pump housing 22. Said pump housing also encloses a button cell 21, such as a silver oxide or alkaline cell, which are readily available commercial cells.

The negative pole of said button cell contacts the cathode 20. Spacer 28 comprised of an electrical insulator prevents contact between the button cell 21 and the pump housing 22. The cathode cap 14 and the spacer 28 are crimped by the pump housing 22 to form a seal. Optionally, spacer 27 and spacer 28 may be integrated into one pan. The contact clip 23 completes the circuit after an electronic insulating pull tab 24 is removed by the user at the time of activation. Fluid to be dispensed 10 is contained between a flexible diaphragm 25 and outer shell 26. The gas chamber 8 into which gas is electrochemically introduced is bounded by the diaphragm 8, the gas shell 7, and the pump housing 22.

FIGS. 8A, 8B and 8C are schematics of general examples of the electrochemical portion of the device, where the cathode includes a reducible material.

The figures include regions Z1, Z2, Z'2, Z3, Z'4, Z4, Z5 interfaces Z1/Z2, Z2/Z'2, Z'2/Z3, Z3/Z'4, Z'4/Z4, Z4/Z5. FIG. 8A represents a pre-discharged cell. FIG. 8B represents a discharging cell. FIG. 8C represents a cell which does not require an electrolyte in addition to the anode and cathode since the reaction product formed serves the function of the electrolyte.

Z1 is the anode current collector and must be an electronic conductor, preferably porous. It may also have a porous inner layer and a nonporous outer layer with a single port or multiple ports to allow escape of released oxygen or nitrogen gas at particular locations. Z1 material must be non-reactive with material Z2 and the oxygen or nitrogen which will be released.

Z2 is the anode and must include the gas releasing compound, either $A_xO_y$ or $A'_{\alpha}N_{62}$, and must be an ionic conductor or a mixed conductor.

If $A_xO_y$ or $A'_{\alpha}N_{\beta}$ are ionically conductive and have low electronic conductivity, then material Z2 may consist entirely of those compounds and may be non-porous; in this case, oxidation will occur at the Z1/Z2 interface, A or A' ions will migrate through layers Z2 and Z3 through the Z2/Z3 and Z3/Z4 interfaces. When this occurs, the thickness of the Z2 layer decreases and it is desirable to have the entire assembly in compression to maintain contact. This may be achieved through utilization of one or more springs.

If $A_xO_y$ or $A'_{\alpha}N_{\beta}$ are not ionic conductors, a material which has lower tendency to oxidize relative to $A_xO_y$ or $A'_{\alpha}N_{\beta}$ but which is ionically conductive must be added to material Z2, in addition, an electronic conductor must be added, usually, the electronic conductivity will be higher than the ionic conductivity which results in initial oxidation at the Z2/Z3 interface. As oxidation of $A_xO_y$ or $A'_{\alpha}N_{\beta}$ occurs, a zone Z' is formed where $A_xO_y$ or $A'_{\alpha}N_{\beta}$ has been consumed but includes the ionic and electronic conducting materials which had been added to material Z2. Oxidation continues at the Z2/Z'2 interface as electrons are conducted through Z2 and cations are conducted through Z'2. Oxygen or nitrogen permeates through Z2 and Z1, thus layer Z2 must be porous enough to allow this permeation. Permeation can also be enhanced if necessary by providing small channels in the Z2 material.

Z5 the cathode current collector and is a non-porous electronic conductor which is non reactive with material Z4.

Z4 is the cathode and includes a reducible material. It must either be an anionic conductor, or mixed conductor. Electrons are provided at the Z5/Z4 interface which ultimately reduce the material in Z4 to anions. Usually, electrons are conducted through Z4, initially anions are formed at the Z3/Z4 interface where cations and anions form a reaction product and create a new layer Z'4. Subsequently, anions may be formed at the Z4/Z'4 interface.

Z'4 material must be either conductive to cations so that reaction product forms at the Z4/Z'4 interface, otherwise Z'4 must be conductive to anions so that reaction product forms at the Z3/Z'4 interface.

Z3 is the electrolyte, a layer which is conductive to either cations or anions but which is an electronic insulator. This layer is necessary if both Z2, Z2' (if formed), Z4', and Z4 are all electronic conductors. If any one of those layers is electronically insulating, then layer Z3 is unnecessary since the insulating layer functions as an electrolyte.

An electrolyte referred to herein above as Ag-Nasicon, Li-Nasicon or other Nasicon material is a metal super ion conductor, and has the general formula $Me_{(1+x)}Zr_2Si_xP_{(3-x)}O_{12}$ wherein Me is a metal such as silver, lithium, sodium, copper and the like. The sodium ion version is referred to as Nasicon, which was the earliest material developed. Other cation conductors are referred to as Li-Nasicon, Ag-Nasicon, etc. These metals are monovalent cations in ionic form. Such electrolytes are solid, ceramic-type materials which are well known cation (positive metal ions) conductors, having been used in sodium-sulfur batteries and similar electrochemical cells in which transport of a metal ion from an anode chamber to cathode chamber was desired. In the above-stated formula, the value of x is equal to or less than 3 and equal to or greater than 0. A typical value for x is 2. The various Nasicon-type materials used in the instant examples had a value for x of about 2.

Although the instant invention is illustrated with a fluid dispensing portion consisting of a flexible membrane or flexible sack, it is to be understood that the invention may include pistons, bellows or other components which may be moved by a pressurized gas to dispense fluids, typically liquids, from a dispenser to the external environment.

What is claimed is:

1. A solid state, battery driven, fluid dispensing micropump comprising:

an electrolyte comprising of an ion transport material selected from the class of materials which transport A cations or A' cations;

a solid anode material of the general form $A_xO_y$ or $A'_{\alpha}N_{\beta}$;

wherein A is a cation with an oxidation state of 2y/x as A ions migrate across said ion conducting electrolyte, or as oxygen is released from solid anode ions migrate across said solid ion conducting electrolyte;

wherein A' is a cation of oxidation state $3\beta/\alpha$ as A ions migrate across said ion conducting electrolyte;

wherein O is a oxygen and N is nitrogen and the value for x is 1 to 3 and y is 1 to 4, a is 1 to 3 and $\beta$ is 1 to 3;

a solid cathode material, said cathode material comprising a halogen ionizable to a minus one valence state or a compound consisting of carbon and halogen ionizable to a mixture of carbon and halogen with a valence of minus one state or a Group VIB substance ionizable to a minus two valence state, or where the migrating cations are reduced to elemental state at the cathode;

a fluid containing chamber having a fluid discharge outlet; and duct means providing gas communication between said anode compartment and said fluid containing chamber.

2. Apparatus as set forth in claim 1, wherein solid anode material includes the compound $Cu_2O$.

3. Apparatus as set forth in claim 1, wherein solid cathode material includes copper or graphite or carbon.

4. Apparatus as set forth in claim 1, wherein a component of the solid electrolyte is CuI.

5. Apparatus as set forth in claim 1, wherein a component of the solid electrolyte is $Rb_4Cu_{16}I_7Cl_{13}$.

6. Apparatus as set forth in claim 1, wherein a component of the solid electrolyte is Cu-Nasicon.

7. A solid-state, electrically self-contained, fluid-dispensing micropump comprising:

an electrochemical cell having an anode compartment, a cathode compartment, solid electrolyte separating said anode and cathode compartments;

a solid anode material of the composition $A_xO_y$ or $A'_\alpha N_\beta$, wherein A is a cation of a metal selected from the class consisting of silver and copper;

wherein A' is a cation of a metal selected from the class consisting of sodium and lithium;

wherein O is a oxygen and N is nitrogen and the value for x is 1 to 3 and y is 1 to 4, $\alpha$ is 1 to 3 and $\beta$ is 1 to 3;

an electrolyte consisting essentially of an ion transport material selected from the class of materials which transport A cations or A' cations;

a cathode material in intimate contact with said electrolyte, said cathode material consisting essentially of a halogen ionizable to a minus one valence state or a compound consisting of carbon and halogen ionizable to a mixture of carbon and halogen with valence of minus one state or a Group VIB substance ionizable to a minus two valence state;

an electrical conductor connectable between said anode and cathode materials, which upon connection results in oxygen or nitrogen being released from the anode material as the cation present, A or A' migrates through the electrolyte to react with the cathodic material in a reaction which includes the electrons released at the anode;

a fluid containing chamber having a fluid discharge outlet; and duct means providing gas communication between said anode compartment and said fluid containing chamber.

8. A fluid dispensing micropump comprising:

a miniature, solid-state, self-contained, gas-producing galvanic electrochemical cell;

a fluid-containing chamber having a fluid discharge outlet; and duct means providing gas communication between said cell and said fluid-containing chamber.

* * * * *

UNITED STATES PATENT AND TRADEMARK OFFICE
CERTIFICATE OF CORRECTION

PATENT NO.  : 5,567,287
DATED       : October 22, 1996
INVENTOR(S) : Joshi et al.

It is certified that error appears in the above-identified patent and that said Letters Patent is hereby corrected as shown below:

On Title Page, under "Assignee" change "Salt Lake" to --Salt Lake City--;

In Column 1, line 56, change "am" to --an--;

In Column 2, line 10, change "Nation" to --Nafion--;

In Column 3, line 15, change "A'N$_{62}$" to A'$_\alpha$N$_\beta$.

In Column 7, line 14, change "of a" to --of an--;

In Column 7, line 27, change "of a" to --of an--;

In Column 9, line 44, change "Li3N" to --Li$_3$N--;

In Column 10, line 39, change "be may" to --may be--;

In Column 11, line 12, change "A$^I_{\alpha N62}$" to -- A$^I_\alpha$N$_\beta$--;

In Column 11, line 32, change "pan" to --part--;

In Column 11, line 57, change "A$^I_\alpha$N$_{62}$" to -- A$^I_\alpha$N$_\beta$--;

In Column 12, line 16, after "Z5" insert --is--;

In Column 13, line 5, change "a oxygen" to --an oxygen--;

In Column 13, line 6, change "a is 1 to 3" to --$\alpha$ is 1 to 3--;

In Column 14, line 3, change "a oxygen" to --an oxygen--.

Signed and Sealed this

Twelfth Day of May, 1998

Attest:

BRUCE LEHMAN

*Attesting Officer*    *Commissioner of Patents and Trademarks*